US010925918B2

(12) United States Patent
Oda et al.

(10) Patent No.: US 10,925,918 B2
(45) Date of Patent: Feb. 23, 2021

(54) COMPOSITION FOR FOOD AND FAT ABSORPTION INHIBITOR

(71) Applicant: FUJIFILM Corporation, Tokyo (JP)

(72) Inventors: Yuriko Oda, Kanagawa (JP); Fumitaka Ueda, Kanagawa (JP)

(73) Assignee: FUJIFILM Cornoration, Tokyo (JP)

( * ) Notice: Subject to any disclaimer, the term of this patent is extended or adjusted under 35 U.S.C. 154(b) by 659 days.

(21) Appl. No.: 14/601,362

(22) Filed: Jan. 21, 2015

(65) Prior Publication Data

US 2015/0132338 A1 May 14, 2015

Related U.S. Application Data

(63) Continuation of application No. PCT/JP2013/072603, filed on Aug. 23, 2013.

(30) Foreign Application Priority Data

Sep. 25, 2012 (JP) .................. 2012-211331

(51) Int. Cl.
| | | |
|---|---|---|
| *A61K 36/82* | (2006.01) | |
| *A61K 36/02* | (2006.01) | |
| *A23F 3/30* | (2006.01) | |
| *A23L 33/105* | (2016.01) | |
| *A23F 3/18* | (2006.01) | |
| *A61K 36/03* | (2006.01) | |
| *A61K 36/37* | (2006.01) | |
| *A23P 10/28* | (2016.01) | |
| *A23L 17/60* | (2016.01) | |

(52) U.S. Cl.
CPC .............. *A61K 36/82* (2013.01); *A23F 3/18* (2013.01); *A23F 3/30* (2013.01); *A23L 33/105* (2016.08); *A61K 36/02* (2013.01); *A61K 36/03* (2013.01); *A61K 36/37* (2013.01); *A23L 17/60* (2016.08); *A23P 10/28* (2016.08); *A23V 2002/00* (2013.01)

(58) Field of Classification Search
None
See application file for complete search history.

(56) References Cited

U.S. PATENT DOCUMENTS

| | | | | |
|---|---|---|---|---|
| 7,939,559 | B2 * | 5/2011 | Nakai .................. | C07D 493/14 514/456 |
| 2006/0134299 | A1 | 6/2006 | Lahteenmaki | |
| 2007/0053929 | A1 | 3/2007 | Funayama et al. | |
| 2009/0156662 | A1 | 6/2009 | Nozawa et al. | |
| 2010/0261784 | A1 * | 10/2010 | Ueda ..................... | A61K 9/2054 514/456 |
| 2012/0276081 | A1 * | 11/2012 | Oda ........................ | A23L 33/18 424/115 |
| 2013/0059817 | A1 * | 3/2013 | Chong .................... | A23L 33/28 514/58 |
| 2014/0127297 | A1 | 5/2014 | Didden | |

FOREIGN PATENT DOCUMENTS

| | | | | |
|---|---|---|---|---|
| CA | 2487588 | A1 * | 12/2003 | ............. A23L 2/38 |
| CA | 2548899 | A1 * | 6/2005 | ............. A61K 36/03 |
| CN | 101888848 | A | 11/2010 | |
| EP | 1693084 | A1 | 8/2006 | |
| JP | 06166618 | A | 6/1994 | |
| JP | 2000152744 | A | 6/2000 | |
| JP | 2002-326932 | A | 11/2002 | |
| JP | 2002326932 | A * | 11/2002 | |
| JP | 2005-170836 | A | 6/2005 | |
| JP | 2005-527234 | A | 9/2005 | |
| JP | WO 2009031690 | A2 * | 3/2009 | ............. A61K 31/05 |
| JP | 2009137899 | A | 6/2009 | |
| JP | 2011-032171 | A | 2/2011 | |
| JP | 2011032171 | A * | 2/2011 | |
| JP | 2011-173847 | A | 9/2011 | |
| JP | 2011173847 | A * | 9/2011 | ............. A61K 36/18 |
| WO | 2007/125644 | A1 | 11/2007 | |
| WO | 2009/031690 | A2 | 3/2009 | |
| WO | 2012/120236 | A1 | 9/2012 | |

OTHER PUBLICATIONS

Chater et al. (2016) J. Appl. Phycol. 28: 1303-1313.*
Kishino et al. (2006) J. Nutr. 136: 433-439.*
Ozaki et al. (2008) J. Nat. Prod. 71, 981-984.*
Sabu et al. (2002) J. Ethnopharmacology 83: 109-116.*
Tsuneki et al. (2004) BMC Pharmacology 4:18 (10 pages).*
Venables et al. (2008) Am. J. Clin. Nutr. 87: 778-84.*
Yoshikawa et al. (2002) J. Nutr. 132: 1819-1824.*
Zhang et al. (2007) Can. J. Physiol. Pharmacol. 85: 1116-1123.*
Notice of Opinion of First Examination, dated Aug. 25, 2015, issued in corresponding CN Application No. 201380037950.5, 19 pages in English and Chinese.
Communication dated Dec. 1, 2015, issued by the Japan Patent Office in corresponding Japanese Application No. 2012-211331, 6 pages in Japanese and English.
Database GNDP [Online] Mintel; Feb. 1, 2011 (Feb. 1, 2011), "Power Bikini Lighten Drink", XP-002753932, Database accession No. 1484074, 3 pages total.
Communication dated Feb. 19, 2016, issued by the European Patent Office in corresponding European Application No. 13842323.1.
Communication dated Mar. 17, 2016 from the Intellectual Property Office of the P.R.C. issued in corresponding Application No. 201380037950.5.
Communication dated Jun. 14, 2016, from the Japanese Patent Office in counterpart application No. 2012-211331.
Br. phycol. J., Jun. 1, 1984, vol. 19, No. 2, pp. 189-202, p. 189 "Inhibitors of mammalian digestive enzymes and polyphenols in some brown marine algae".
The Third Office Action, dated Sep. 14, 2016, issued in corresponding CN Application No. 201380037950.5, 30 pages in English and Chinese.

(Continued)

*Primary Examiner* — Russell G Fiebig

(74) *Attorney, Agent, or Firm* — Sughrue Mion, PLLC

(57) ABSTRACT

A composition for food and a fat absorption inhibitor, each including a seaweed polyphenol and a tea extract.

12 Claims, No Drawings

(56) References Cited

OTHER PUBLICATIONS

Communication dated Jan. 10, 2017, from the Japanese Patent Office in counterpart application No. 2012-211331.
International Search Report for PCT/JP2013/072603 dated Oct. 22, 2013, 7 pages in Japanese and English.
Written Opinion for PCT/JP2013/072603 dated Oct. 22, 2013, 7 pages in Japanese and English.
Decision of Rejection, dispatched May 10, 2017, in corresponding CN Application No. 201380037950.5, 20 pages in English and Chinese.
Trial Decision dated May 8, 2018, from the Japanese Patent Office in counterpart Japanese Application No. 2012-211331.

* cited by examiner

COMPOSITION FOR FOOD AND FAT ABSORPTION INHIBITOR

CROSS-REFERENCE TO RELATED APPLICATIONS

This application is a continuation application of International Application No. PCT/JP2013/072603, filed Aug. 23, 2013, the disclosure of which is incorporated herein by reference in its entirety. Further, this application claims priority from Japanese Patent Application No. 2012-211331, filed Sep. 25, 2012, the disclosure of which is incorporated herein by reference in its entirety.

TECHNICAL FIELD

The present invention relates to a composition for food and a fat absorption inhibitor.

BACKGROUND ART

In recent years, an environment is provided in which excessive fat ingestion easily occurs due to dietary life centered on high fat food introduced by westernization of diet. For this reason, drugs or food materials that inhibit fat absorption have attracted attention.

For example, International Publication No. WO 2007/125644 discloses a composition for inhibiting fat absorption that includes a mixture of four components—theaflavin monogallate, a theaflavin, theaflavin digallate, and polyphenol.

Japanese Patent Application Laid-Open (JP-A) No. 2005-170836 discloses a lipase inhibitor that includes, as an active ingredient, an extract of *Ascophyllum nodosum*, which is a brown algae corresponding to one type of marine algae.

In particular, it is known that the extract of *Ascophyllum nodosum* is a component referred to as "seaweed polyphenol" and has a favorable lipase inhibitory activity.

SUMMARY OF INVENTION

Technical Problem

However, the inventors of the present application found that intake of a composition or component having an fat absorption inhibitory effect as a food material deteriorates the intestinal environment. Compositions having a fat absorption inhibitory effect that does not deteriorate the intestinal environment are not known.

Therefore, the present invention addresses provision of a composition for food and a fat absorption inhibitor that can effectively inhibit fat absorption without deteriorating the intestinal environment.

Solution to Problem

According to aspects of the invention, a composition for food, a fat absorption inhibitor, and a method of inhibiting fat absorption as described below are provided.

[1] A composition for food including a seaweed polyphenol and a tea extract.

[2] The composition for food according to [1], further including an extract of a plant of the genus *Salacia*.

[3] The composition for food according to [2], in which the extract of a plant of the genus *Salacia* has a half-maximal (50%) inhibitory concentration ($IC_{50}$ value) against sucrase of 2000 µg/ml or less.

[4] The composition for food according to any one of [1] to [3], in which the seaweed polyphenol is a brown algae-derived polyphenol.

[5] The composition for food according to any one of [1] to [4], in which the tea extract is a green tea extract.

[6] The composition for food according to any one of [1] to [5], which is in tablet form or capsule form.

[7] The composition for food according to any one of [1] to [6], in which the seaweed polyphenol has a half-maximal (50%) inhibitory concentration ($IC_{50}$ value) against lipase of from 0.0001 µg/ml to 50 µg/ml.

[8] The composition for food according to any one of [1] to [7], in which a ratio (mass ratio) of the tea extract to the seaweed polyphenol is from 100 to 0.01.

[9] A fat absorption inhibitor including a seaweed polyphenol and a tea extract.

[10] The fat absorption inhibitor according to [9], further including an extract of a plant of the genus *Salacia*.

[11] The fat absorption inhibitor according to [10], in which the extract of a plant of the genus *Salacia* has a half-maximal (50%) inhibitory concentration ($IC_{50}$ value) against sucrase of 2000 µg/ml or less.

[12] The fat absorption inhibitor according to any one of [9] to [11], in which the seaweed polyphenol is a brown algae-derived polyphenol.

[13] The fat absorption inhibitor according to any one of [9] to [12], in which the tea extract is a green tea extract.

[14] The fat absorption inhibitor according to any one of [9] to [13], which is in tablet form or capsule form.

[15] The fat absorption inhibitor according to any one of [9] to [14], in which the seaweed polyphenol has a half-maximal (50%) inhibitory concentration ($IC_{50}$ value) against lipase of from 0.0001 µg/ml to 50 µg/ml.

[16] The fat absorption inhibitor according to any one of [9] to [15], in which a ratio (mass ratio) of the tea extract to the seaweed polyphenol is from 100 to 0.01.

[17] A method of inhibiting fat absorption, the method including administrating the fat absorption inhibitor according to any one of [9] to [16] to a subject in need of inhibition of fat absorption.

[18] Use of a seaweed polyphenol and a tea extract in the manufacture of a fat absorption inhibitor.

[19] Use of a seaweed polyphenol, a tea extract, and an extract of a plant of the genus *Salacia* in the manufacture of a fat absorption inhibitor.

[20] The use in the manufacture of the fat absorption inhibitor according to [18] or [19], in which the seaweed polyphenol is a brown algae-derived seaweed polyphenol.

Advantageous Effects of Invention

According to the invention, a composition for food and fat absorption inhibitor that can effectively inhibit fat absorption without deteriorating the intestinal environment can be provided.

DESCRIPTION OF EMBODIMENTS

The composition for food according to the invention is a composition for food including a seaweed polyphenol and a tea extract.

In the composition for food according to the invention, inclusion of a seaweed polyphenol and a tea extract enables effective inhibition of fat absorption without deteriorating the intestinal environment. We presume that the reason therefor is as follows. Specifically, a seaweed polyphenol ingested inhibits fat absorption due to the fat absorption inhibitory effect of the seaweed polyphenol, as a result of which fat accumulates in the intestine. The accumulation in turn results in proliferation of harmful intestinal bacteria (e.g., bacteria of the genus *Clostridium*, bacteria of the genus *Enterobacter*) and the like. The harmful intestinal bacteria produce gas, which cause sensation of abdominal bloating. Furthermore, the proliferation of the harmful intestinal bacteria reduces bowel movement and thus deterioratess the intestinal environment. The tea extract can alleviate the sensation of abdominal bloating and improve the bowel movement. However, the invention is not constrained by such presumption.

The term "process" as used herein indicates not only a separate process but also a process that is not clearly distinguished from other processes as long as the desired effect of the process is obtained therefrom.

In this specification, each numerical range specified using "(from) . . . to . . . " represents a range including the numerical values noted before and after "to" as the minimum value and the maximum value, respectively.

Furthermore, in reference to the amount of each ingredient in the composition, when the composition includes plural substances corresponding to a particular ingredient, the amount of the particular ingredient noted in this specification means the total amount of the plural substances in the composition unless otherwise specified.

Hereinbelow, the invention is described in detail.

In the invention, the seaweed polyphenol is used as a generic name for a polyphenol extracted from a seaweed or a polyphenol-containing fraction extracted from a seaweed, and the seaweed polyphenol includes a phlorotannin compound (e.g., phloroglucinol or a polymer thereof) as a main component. The seaweed polyphenol is preferably a brown algae-derived polyphenol. Examples of the brown algae include brown seaweeds of the genus *Ascophyllum, Laminaria, Sargassum, Eisenia bicyclis, Ecklonia cava*, and *Ecklonia kurome*. From the viewpoint of the fat absorption inhibitory effect, the brown algae is preferably a seaweed of the genus *Ascophyllum*, particularly *Ascophyllum nodosum*.

As an extraction solvent that may be used for extracting the seaweed polyphenol, water or an organic solvent, or a mixed solution thereof is used. Examples of the organic solvent include polar organic solvents including lower alcohols having from 1 to 4 carbon atoms such as methanol, ethanol, propanol, isopropanol, n-butanol, isobutanol, sec-butanol, and tert-butanol, and ketones such as dimethyl ketone, methyl ethyl ketone, acetone, and methyl isobutyl ketone; and non-polar organic solvents such as methyl acetate, ethyl acetate, butyl acetate, and diethyl ether. A mixed product obtained by appropriately combining a polar organic solvent, such as those described above, and a non-polar organic solvent, such as those described above, is also usable. Examples of extraction methods usable for obtaining the extract include known methods such as immersion extraction, heat extraction, continuous extraction, and supercritical extraction. The extract may subsequently be concentrated using known methods. The obtained extract, concentrate or the like may be further purified using known methods. Examples of purification methods include ultrafiltration, adsorption resin treatment, molecule chromatography, partition chromatography, and liquid-liquid extraction. In the invention, it is preferable that the seaweed polyphenol has a lipase inhibitory activity. Examples of methods usable for preparation of the seaweed polyphenol include the method described in paragraphs [0017], [0018], and [0021] of JP-A No. 2005-170836.

From the viewpoint of the fat absorption inhibitory effect, the seaweed polyphenol has a half-maximal (50%) inhibitory concentration ($IC_{50}$ value) against lipase of preferably from 0.0001 µg/ml to 50 µg/ml, and more preferably from 0.001 µg/ml to 10 µg/ml. In a case in which the $IC_{50}$ value against lipase is 50 µg/ml or less, a more favorable inhibitory effect on fat absorption can be obtained. The half-maximal (50%) inhibitory concentration against lipase may be measured, for example, according to the method described in paragraph [0019] of JP-A No. 2005-170836. The $IC_{50}$ value of the seaweed polyphenol against lipase may vary according to, for example, the method employed for extracting the extract.

As the seaweed polyphenol in the invention, a commercially available product with a desired half-maximal (50%) inhibitory concentration against lipase may be used, as appropriate. Examples of the commercially available product include "Seaweed Polyphenol" (derived from *Ascophyllum nodosum*, RIKEN VITAMIN Co., Ltd.).

The content of seaweed polyphenol in the composition for food varies according to the dosage form or the administration manner of the composition for food. The content of seaweed polyphenol in the composition for food is not particularly limited as long as the amount is effective in inhibiting fat absorption. In a case in which the composition for food is in solution form, the content of seaweed polyphenol in the composition for food may be set to be, for example, from 0.00001% by mass to 10% by mass, and preferably from 0.00001% by mass to 5% by mass, with respect to the total mass of the composition. In a case in which the composition for food is in solid form, the content of seaweed polyphenol in the composition for food may be set to be, for example, from 0.001% by mass to 50% by mass, preferably from 0.01% by mass to 20% by mass, and more preferably from 0.1% by mass to 5% by mass, with respect to the total mass of the composition. The dose of the composition for food is not particularly limited and varies according to the dosage form or the like. In general, the dose of the composition for food in the case of single daily dosing may be from 1 mg to 500 mg, and preferably from 5 mg to 200 mg, in terms of the seaweed polyphenol dose.

The tea extract in the invention is an extract obtained from a tea plant, which is an evergreen tree of the Theaceae family. As the tea plant, both of *Camellia assamica*, which are cultivated in India, Sri Lanka, and south-eastern Asia, and *Camellia sinensis*, which are cultivated in China and Japan, are usable. The tea extract is preferably a green tea extract from the viewpoint of the effect with respect to improvement of the intestinal environment.

In general, the extraction of the tea extract is preferably conducted using water, alcohol, or a hydrous alcohol as an extraction solvent. The extraction solvent to be used is more preferably hot water, ethanol, or hydrous ethanol. The alcohol concentration in the hydrous alcohol may be set to be from 30% by mass to 90% by mass, and preferably from 40% by mass to 70% by mass, with respect to the total mass of the hydrous alcohol. Examples of methods usable for drying include, but not limited to, spray drying and freeze drying.

The tea extract preferably includes an antioxidative substance such as a polyphenol or a catechin. More specifically, the tea extract preferably inclures catechin, epicatechin, gallocatechin, epigallocatechin, catechin gallate, epicatechin gallate, gallocatechin gallate, or epigallocatechin gallate, or a combination of two or more thereof, and more preferably includes epigallocatechin gallate.

The content of tea extract in the composition for food varies according to the dosage form or the administration manner of the composition for food, and is not particularly limited. The content of tea extract in the composition for food may be any content which can improve the intestinal environment in relation to the seaweed polyphenol. In a case in which the composition for food is in solution form, the content of tea extract in the composition for food may be set to 0.0001% by mass to 20% by mass, and preferably 0.001% by mass to 10% by mass, with respect to the total mass of the composition. In a case in which the composition for food is in solid form, the content of tea extract in the composition for food may be set to be from 0.5% by mass to 80% by mass, preferably from 1% by mass to 70% by mass, and more preferably from 5% by mass to 30% by mass, with respect to the total mass of the composition.

In the composition for food according to the invention, the ratio of tea extract to seaweed polyphenol (tea extract/seaweed polyphenol, in terms of mass ratio) may vary according to the levels of concentration of the respective components. The ratio of tea extract/seaweed polyphenol in the composition for food may be set to be preferably from 100 to 0.01, more preferably from 80 to 0.05, still more preferably from 50 to 3, and even more preferably from 15 to 3. In a case in which the tea extract/seaweed polyphenol ratio in the composition for food is set to be 0.01 or more, a more favorable effect with respect to improvement of the intestinal environment can be produced.

The composition for food according to the invention may further include an extract of a plant of the genus *Salacia*. In a case in which the composition for food further includes an extract of a plant of the genus *Salacia*, further improvement of the intestinal environment, including bowel movement improvement and/or fecal properties, can be achieved.

The plant of the genus *Salacia* is a plant of *Celastraceae* that grows wild mainly in Sri Lanka, India, and southeastern Asia, and the plant is more specifically at least one plant selected from the group consisting of *Salacia reticulata*, *Salacia oblonga*, *Salacia prinoides*, and *Salacia chinensis*. Examples of the extract of a plant of the genus *Salacia* that may be contained in the composition for food include an extract obtained by extraction from a pulverized product of the whole plant body of a plant of the genus *Salacia*, and an extract (preferably, an extract powder) obtained from a portion, such as a root, a trunk, a leaf, a flower or a fruit, of the plant. It is also contemplated that one or more portions of the plant may be mixed and used. The extract of a plant of the genus *Salacia* for use is more preferably an extract obtained by extraction from a root or a trunk.

In a case in which an extract of a plant of the genus *Salacia* is used, the extract is preferably an extract obtained by drying a product which in turn is obtained from the whole plant or any of the portions of the plant by extraction with a solvent. The extraction solvent may be selected from water, an alcohol such as methanol or ethanol, or a mixed solvent of water with an alcohol or ketone such as acetone. The extraction solvent to be used is preferably water, an alcohol, or a hydrous alcohol. The extraction solvent to be used is more preferably hot water, ethanol, or hydrous ethanol. The alcohol concentration in the hydrous alcohol may be set to be from 30% v/v to 90% v/v, and preferably from 40% v/v to 70% v/v. Examples of drying methods include, but not limited to, spray drying and freeze drying.

The extract of a plant of the genus *Salacia* according to the invention preferably has a half-maximal (50%) inhibitory concentration ($IC_{50}$ value) against sucrase of 2,000 μg/ml or less. A half-maximal (50%) inhibitory concentration of the extract of a plant of the genus *Salacia* against sucrase of 2,000 μg/ml or less ensures an increase in the number of beneficial intestinal bacteria such as bacteria of the genus *Bifidobacterium* (sometimes simply referred to as "bifidobacteria"), and enables the intestinal environment to be more improved. The half-maximal (50%) inhibitory concentration against sucrase may be set to be preferably from 0.001 μg/ml to 1,500 μg/ml, more preferably from 0.05 μg/ml to 1,000 μg/ml, and still more preferably from 0.05 μg/ml to 800 μg/ml. The half-maximal (50%) inhibitory concentration against sucrase may be measured according to the method described in paragraphs [0009] to [0012] of JP-A No. 2009-249315.

The composition for food according to the invention may further include a component, other than the above-described components, that can improve the intestinal environment. Examples of the component that improves the intestinal environment include yoghurt and oligosaccharide.

The composition for food according to the invention may further include at least one selected from the group consisting of calcium carbonate and silicon dioxide. The inclusion of such a substance can prevent discoloration over time of components contained in the composition for food. In particular, in a case in which the composition for food contains an extract of a plant of the genus *Salacia*, the inclusion can prevent discoloration over time of the extract of a plant of the genus *Salacia*. The silicon dioxide is preferably fine silicone dioxide in powder form.

The content of calcium carbonate or silicon dioxide in the composition varies according to the dosage form of the composition. In a case in which the dosage form for the composition is a tablet or a hard capsule, the content of calcium carbonate is preferably from 0.1% by mass to 10% by mass with respect to the composition, and the content of silicon dioxide is preferably from 0.5% by mass to 20% by mass with respect to the composition. In a case in which calcium carbonate and silicon dioxide are used in combination, they may be used at a ratio of calcium carbonate to silicon dioxide in a range of from 1:0.05 to 1:200 in terms of mass ratio.

The composition for food according to the invention may include, besides the above-described components, a carrier acceptable for food applications or a publicly-known or well-known additive agent.

Examples of a carrier preferably used for formulating the composition to have a solution form include aqueous media such as water. Examples of an additive preferably used for formulating the composition to have a solid form include excipients such as crystalline cellulose and magnesium stearate, and swelling agents such as cornstarch and alginic acid. Furthermore, shellac, sugar, a film coating base material, Yeast wrap or the like may be used as a coating agent for tablets, capsules, or granules.

In addition, low hygroscopic raw materials and moisture absorbents usable as foods or food additives may be used. Preferable examples of usable low hygroscopic raw materials include cellulose, crystalline cellulose, cellulose powder, microcrystalline cellulose, lactose, a sugar alcohol, trehalose, magnesium stearate, and calcium stearate. Examples of usable moisture absorbents include silicates, magnesium carbonate, ferrocyanides, and polysaccharides. More preferable examples of usable low hygroscopic raw materials include crystalline cellulose, microcrystalline cellulose, and lactose, and a combination of two or more thereof.

Examples of a compound required for shaping into a powder form, a solid form, or a liquid form include erythritol, maltitol, hydroxypropylcellulose, kaolin, and talc.

A black oolong tea polyphenol, an onion peel extract, a red wine polyphenol, a coffee bean manno-oligosaccharide, Orlistat, a star fruit extract, a wheat extract or the like may further be used as another fat absorption inhibiting component.

The composition for food according to the invention may be formulated into any of the liquid, solid, powder, and gel forms, and may be formulated into a form such as a solution, a tablet, a capsule (hard capsule, soft capsule) or a granule. It is preferable to formulate the composition for food into a tablet or a capsule from the viewpoint of convenience in use.

The fat absorption inhibitor according to the invention includes a seaweed polyphenol and a tea extract. Due to the combined inclusion of a seaweed polyphenol and a tea extract, the fat absorption inhibitor can inhibit fat absorption without deteriorating the intestinal environment, as descried above. The fat absorption inhibitor may further include an extract of a plant of the genus *Salacia*. The inclusion of an extract of a plant of the genus *Salacia* enables improvement of bowel movement, fecal properties, and the like.

With regard to the preparation of the seaweed polyphenol, the tea extract, and the extract of a plant of the genus *Salacia* for use in the fat absorption inhibitor according to the invention, the respective contents of these components in the fat absorption inhibitor, the dosage form of the fat absorption inhibitor, and the like, the same specifics as those described for the composition for food shall apply.

The manner of administering the fat absorption inhibitor according to the invention is preferably oral administration, but may be parenteral administration such as rectal administration or sublingual administration.

In one embodiment of the invention, a method of inhibiting fat absorption is provided which includes administrating a fat absorption inhibitor that includes a seaweed polyphenol and a tea extract to a subject in need of inhibition of fat absorption. Using this method, the absorption of fat into the body can be inhibited without deteriorating the intestinal environment. Examples of the subject to which the fat absorption inhibitor is administered include a mammal such as human.

In another embodiment of the invention, use of a seaweed polyphenol and a tea extract in the manufacture of a fat absorption inhibitor, and use of a seaweed polyphenol, a tea extract, and an extract of a plant of the genus *Salacia* in the manufacture of a fat absorption inhibitor, are also provided.

The composition for food and the fat absorption inhibitor according to the invention can inhibit fat absorption without deteriorating the intestinal environment. Therefore, the composition for food and the fat absorption inhibitor are expected to ameliorate life-style related diseases or obesity, and to exert effect with respect to the prevention or treatment of various symptoms or diseases associated with aging. Furthermore, the composition for food and the fat absorption inhibitor are expected to also exert effects with respect to weight loss, a decrease in body fat percentage, or the like.

EXAMPLES

Hereinafter, the invention is described in detail with reference to examples. However, the invention is not limited to these examples. Here, "%" is based on mass unless otherwise specified.

Examples 1 to 4 and Comparative Examples 1 to 4

The following tests were conducted in order to clarify the effect of a seaweed polyphenol and a tea extract on the intestinal environment.

40 male adults (from age 20 to age 60) were randomly divided into 8 groups each consisting of 5 people. Ingestion test was carried out for one week with respect to the samples designated for the respective groups (Examples 1 to 4 and Comparative Examples 1 to 4). The ingestion was performed by dividing the following one-day dose into three doses and having this ingested. After the intake of the sample, the questionnaire survey on abdominal symptom and fecal properties was carried out. The results are shown in Table 1. In the table, the number of the blend ratio of each component represents a percentage by mass. Here, the amount of the seaweed polyphenol ingested per day was set to 20 mg.

The components used were as follows.

Seaweed polyphenol: a product manufactured by RIKEN VITAMIN Co., Ltd., having an $IC_{50}$ value against lipase of 0.01 µg/ml or less Green tea extract: a commercial product Extract of a plant of the genus *Salacia*: a *Salacia reticulata* extract having an $IC_{50}$ value against sucrase of 200 µg/ml or less $IC_{50}$ value of the extract of a plant of the genus *Salacia* against sucrase and $IC_{50}$ value of each sample against lipase were determined as follows.

(1) Measurement of $IC_{50}$ value against sucrase

Preparation of sample solution: 2 mg of the extract of the plant of the genus *Salacia* was weighed out and put in a tube. 2 mL of water was added thereto, and the resultant mixture was thoroughly suspended to prepare a sample solution having a concentration of 1 mg/mL. The obtained sample solution was diluted with water to varied concentrations of 0, 50, 100, 250, and 500 µg/mL.

Preparation of substrate solution: Sucrose was dissolved in a 0.2 M maleate buffer (pH 6.0) to a sucrose concentration of 100 mM, and the resultant solution was used as a substrate solution.

Preparation of crude enzyme solution: 1 g of intestinal acetone powder rat (manufactured by Sigma-Aldrich Co. LLC.) was suspended in 10 mL of physiological saline, and then the resultant suspension was subjected to centrifugation (3,000 rpm, 4° C., 5 min) The resulting supernatant was separated, and used as a crude enzyme solution.

400 µL of the substrate solution was added to 500 µL each of the above-described sample solutions having the varied concentrations, and the solutions were pre-heated in a water bath at 37° C. for 5 minutes. 100 µL of the crude enzyme solution was added to each of the solutions, and a reaction was allowed to proceed at 37° C. for 60 minutes. After completion of the reaction, the enzyme was inactivated by heating at 95° C. for 2 minutes, thereby terminating the reaction. The concentration of glucose produced was quantitatively determined using a commercially available GLUCOSE CII TEST WAKO kit based on the mutarotase glucose oxidase method (Wako Pure Chemical Industries, Ltd).

Preparation of blank: To 250 µL each of the above-described sample solutions having the varied concentrations, 200 µL of the substrate solution and 50 µL of the crude enzyme solution were added, and the solutions were heated at 95° C. for 2 minutes immediately after the addition of the crude enzyme solution, thereby thermally inactivating the enzyme and obtaining blank data. A calibration curve was obtained based on the obtained values, and a concentration at which the enzyme activity is inhibited by 50% ($IC_{50}$ value) was determined.

(2) Measurement of $IC_{50}$ Value Against Lipase

Preparation of sample solution: 2 mg of the composition for food (Examples 1 to 4, Comparative Examples 1 to 4) was weighed out and put in a tube. 2 mL of water was added thereto, and the resultant mixture was thoroughly suspended to prepare a sample solution having a concentration of 1 mg/mL. The obtained sample solution was diluted with water to varied concentrations of 0, 50, 100, 250, and 500 µg/mL.

Preparation of lipase solution: Lipase from porcine pancreas (Sigma-Aldrich Co. LLC.) was diluted with ultrapure water to prepare a solution having a concentration of 0.1 mg/mL.

Preparation of measurement sample: 10 µL of the lipase solution was added to 100 µL of the sample solution, followed by thorough mixing.

Measurement: Lipase inhibitory activity was quantified using a LIPASE KIT S (DS Pharma Biomedical Co., Ltd.).

The $IC_{50}$ values of the obtained samples against lipase are indicated in Table 1 as relative values with the $IC_{50}$ value of Comparative Example 1 being designated as 1.

The values regarding the abdominal symptom and the fecal properties based on the results of questionnaire survey are as follows.

(1) sensation of abdominal bloating: average of evaluations made by five people with respect to the following:

Not felt: sensation of bloating due to gas generation in the abdomen or the like was not felt;

Moderately felt: sensation of bloating in the abdomen was moderately felt;

Clearly felt: sensation of bloating due to gas generation in the abdomen or the like was clearly felt.

(2) bowel movement: the number of people who did not suffer from constipation or who did not feel a sense of incomplete evacuation after defecation.

(3) fecal properties:

Normal: slightly brownish-ocher colored feces; it required a certain period of time for the feces to collapse when the feces immersed in water after defecation.

Good: ocher colored feces; it took a shorter time for the feces to collapse when immersed in water after defecation, than that in the case of the feces evaluated as "Normal".

Bad: brown colored feces; it took a longer time for the feces to collapse when immersed in water after defecation, than that in the case of the feces evaluated as "Normal".

As shown in Table 1, in the cases of the compositions according to Examples 1 to 4, each of which includes a seaweed polyphenol and a green tea extract, sensation of abdominal bloating was not felt, and favorable bowel movement was achieved. In contrast, in the case of Comparative Example 1, in which only a seaweed polyphenol was included, there was a tendency toward sensation of abdominal bloating, deteriorated bowel movement, and constipation. In Comparative Examples 2 to 4, in which an extract of a plant of the genus *Salacia*, yogurt, or an oligosaccharide was added, instead of the tea extract, to a seaweed polyphenol, the sensation of abdominal bloating was not eliminated, and bowel movement was not superior to that of Examples 1 to 4. As demonstrated above, it was found that the compositions according to Examples provide a fat absorption inhibitory effect exerted by the seaweed polyphenol, without deteriorating the intestinal environment.

As demonstrated in Table 2, it was also found that inclusion of an extract of a plant of the genus *Salacia* in addition to a seaweed polyphenol and a green tea extract enables further improvement of the intestinal environment in terms of bowel movement and fecal properties.

Therefore, according to the invention, fat absorption can be inhibited without deteriorating the intestinal environment.

REFERENCE EXAMPLES

The effect of an extract of a plant of the genus *Salacia* with respect to the proliferation of intestinal bifidobacteria (bacteria of the genus *Bifidobacterium*) was determined as follows.

Samples of the extract of the plant of the genus *Salacia* having half-maximal (50%) inhibitory concentrations ($IC_{50}$ values) against sucrase ranging from 0 µg/ml to 2,000 µg/ml were prepared by appropriately mixing the extract of the plant of the genus *Salacia* (extract powder) and a crystalline cellulose.

Each of the samples was subjected to an ingestion test using 21 healthy adults as subjects. Feces were collected before the ingestion test and after 4 weeks of ingestion, and the ratio of bacteria of the genus *Bifidobacterium* therein (bifidobacteria after intake/bifidobacteria before intake) was determined using a TRFLP method. The results are indicated in Table 2. The numbers indicated in Table 2 represent relative values, assuming that the ratio of bacteria of the genus *Bifidobacterium* observed for a sample having an $IC_{50}$ value against sucrase of 5,000 µg/ml is 1.

TABLE 1

|  | Ex. 1 | Ex. 2 | Ex. 3 | Ex. 4 | Comp. Ex. 1 | Comp. Ex. 2 | Comp. Ex. 3 | Comp. Ex. 4 |
|---|---|---|---|---|---|---|---|---|
| Seaweed polyphenol (% by mass) | 2 | 2 | 2 | 2 | 2 | 2 | 2 | 2 |
| Green tea extract (% by mass) | 15 | 15 | 15 | 15 | | | | |
| Extract of plant of genus *Salacia* (% by mass) | | 25 | | | | 25 | | |
| Yogurt (% by mass) | | | 15 | | | | 15 | |
| Oligosaccharide (% by mass) | | | | 15 | | | | 15 |
| Water | balance | balance | balance | balance | balance | balance | balance | balance |
| Abdominal symptom | | | | | | | | |
| Sensation of abdominal bloating | Not felt | Not felt | Not felt | Not felt | Clearly felt | Moderately felt | Clearly felt | Clearly felt |
| Bowel movement | 3 | 5 | 3 | 4 | 0 | 3 | 2 | 2 |
| Fecal properties | Normal | Good | Normal | Normal | Bad | Normal | Bad | Bad |
| $IC_{50}$ value of lipase | 1 | 1 | 0.8 | 1 | 1 | 1 | 0.8 | 1 |

Ex.: Example;
Comp. Ex.: Comparative Example

TABLE 2

| Types of extract of plant of genus Salacia (IC$_{50}$ value [µg/ml]) | Relative ratio of bifidobacteria |
|---|---|
| 5000 | 1.0 |
| 2200 | 0.9 |
| 2000 | 1.4 |
| 800 | 3.3 |
| 400 | 4.0 |
| 200 | 4.2 |
| 100 | 4.1 |

As demonstrated in Table 2, it was found that extracts of the plant of the genus *Salacia* having IC$_{50}$ values against sucrase of 2,000 µg/ml or less, particularly from 100 µg/ml to 800 µg/ml, have a high potential to proliferate bacteria of the genus *Bifidobacterium*, which are beneficial intestinal bacteria. Accordingly, it is understood that use of an extract of a plant of the genus *Salacia* having an IC$_{50}$ value against sucrase of 2,000 µg/ml or less results in the proliferation of bacteria of the genus *Bifidobacterium*, which are beneficial intestinal bacteria, thereby improving the intestinal environment.

Examples of Formulation

Examples of the composition for food and the fat absorption inhibitor according to the invention are illustrated below. In the following formulations, the extract of the plant of the genus *Salacia* used in Example 2 may be used as an extract of a plant of the genus *Salacia*, and the seaweed polyphenol used in Example 1 may be used as seaweed polyphenol. The capsule formulation is obtained by filling a filling composition that includes the components as listed in the following formulation into the interior of a gelatin capsule film, using a conventional method.

The use of such compositions for food enables inhibition of fat absorption without deterioration of the intestinal environment.

(1) Tablet

| Component | Addition amount (% by mass) |
|---|---|
| extract of plant of genus *Salacia* | 25.0 |
| red wine polyphenol | 10.0 |
| onion peel extract powder | 6.0 |
| green tea extract | 15.0 |
| seaweed polyphenol | 2.0 |
| chromium yeast | 4.0 |
| long pepper extract powder | 1.0 |
| red pepper powder | 1.0 |
| crystalline cellulose | 30.0 |
| sucrose fatty acid ester | 2.0 |
| lactose | 1.0 |
| calcium carbonate | 1.0 |
| silicon dioxide fine particles | 2.0 |

(2) Capsule Formulation (Filling Composition)

| Component | Addition amount (% by mass) |
|---|---|
| extract of plant of genus *Salacia* | 25.0 |
| red wine polyphenol | 10.0 |
| onion peel extract powder | 6.0 |
| green tea extract | 15.0 |
| seaweed polyphenol | 2.0 |
| chromium yeast | 4.0 |
| long pepper extract powder | 1.0 |
| red pepper powder | 1.0 |
| crystalline cellulose | 33.0 |
| calcium carbonate | 1.0 |
| silicon dioxide fine particles | 2.0 |

The disclosure of Japanese Patent Application No. 2012-211331, filed Sep. 25, 2012, is incorporated herein by reference in its entirety.

All publications, patent applications, and technical standards mentioned in this specification are herein incorporated by reference to the same extent as if each individual publication, patent application, or technical standard was specifically and individually indicated to be incorporated by reference.

The invention claimed is:

1. A beneficial bacteria proliferating composition, comprising effective amounts of: a seaweed polyphenol derived from a brown seaweed of the genus *Ascophyllum*, a green tea extract, and an extract of a plant of the genus *Salacia*, wherein:
   the seaweed polyphenol has a half-maximal (50%) inhibitory concentration (IC$_{50}$ value) against lipase of 0.01 µg/ml or lower,
   the extract of a plant of the genus *Salacia* has a half-maximal (50%) inhibitory concentration (IC$_{50}$ value) against sucrase of 200 µg/ml or less,
   the mass ratio of the green tea extract to the seaweed polyphenol (green tea extract/seaweed polyphenol) is from 15 to 0.05, and
   the composition is in a tablet or a capsule, containing an excipient to prevent discoloration.

2. A beneficial bacteria proliferating fat absorption inhibitor comprising effective amounts of: a seaweed polyphenol derived from a brown seaweed of the genus *Ascophyllum*, a green tea extract, and an extract of a plant of the genus *Salacia*, wherein:
   the seaweed polyphenol has a half-maximal (50%) inhibitory concentration (IC$_{50}$ value) against lipase of 0.01 µg/ml or lower,
   the extract of a plant of the genus *Salacia* has a half-maximal (50%) inhibitory concentration of (IC$_{50}$ value) against sucrase of 200 µg/ml or less,
   the mass ratio of the green tea extract to the seaweed polyphenol (green tea extract/seaweed polyphenol) is from 15 to 0.05, and
   the inhibitor is present in a tablet or a capsule, containing an excipient to prevent discoloration.

3. A method of inhibiting fat absorption, the method comprising administering an effective amount of the fat absorption inhibitor according to claim 2 to a subject in need of inhibition of fat absorption.

4. The method of inhibiting fat absorption according to claim 3, wherein the fat absorption inhibitor further comprises an extract of a plant of the genus *Salacia*.

5. The method of inhibiting fat absorption according to claim 4, wherein the extract of a plant of the genus *Salacia* has a half-maximal (50%) inhibitory concentration (IC$_{50}$ value) against sucrase of 2000 µg/ml or less.

6. The method of inhibiting fat absorption according to claim 3, wherein the seaweed polyphenol is a brown algae-derived polyphenol.

7. The method of inhibiting fat absorption according to claim 3, wherein the tea extract is a green tea extract.

8. The method of inhibiting fat absorption according to claim 3, wherein the fat absorption inhibitor is in a tablet form or capsule form.

9. A beneficial intestinal bacteria proliferating composition, comprising effective amounts of: a seaweed polyphenol derived from a brown seaweed of the genus *Ascophyllum*, a green tea extract, and an extract of a plant of the genus *Salacia*, wherein:
- the seaweed polyphenol has a half-maximal (50%) inhibitory concentration ($IC_{50}$ value) against lipase of 0.01 µg/ml or lower,
- the extract of a plant of the genus *Salacia* has a half-maximal (50%) inhibitory concentration ($IC_{50}$ value) against sucrase of 200 µg/ml or less,
- the mass ratio of the green tea extract to the seaweed polyphenol (green tea extract/seaweed polyphenol) is from 15 to 0.05, and
- the composition is in a tablet or a capsule containing an excipient to prevent discoloration.

10. The beneficial intestinal bacteria proliferating composition according to claim 9, wherein the beneficial intestinal bacteria is *bifidobacterium* or *lactobacillus*.

11. A beneficial intestinal bacteria proliferating fat absorption inhibitor, comprising effective amounts of: a seaweed polyphenol derived from a brown seaweed of the genus *Ascophyllum*, a green tea extract, and an extract of a plant of the genus *Salacia*, wherein:
- the seaweed polyphenol has a half-maximal (50%) inhibitory concentration ($IC_{50}$ value) against lipase of 0.01 µg/ml or lower,
- the extract of a plant of the genus *Salacia* has a half-maximal (50%) inhibitory concentration ($IC_{50}$ value) against sucrase of 200 µg/ml or less,
- the mass ratio of the green tea extract to the seaweed polyphenol (green tea extract/seaweed polyphenol) is from 15 to 0.05, and
- the inhibitor is in a tablet or a capsule containing an excipient to prevent discoloration.

12. The beneficial intestinal bacteria proliferating fat absorption inhibitor according to claim 11, wherein the beneficial intestinal bacteria is *bifidobacterium* or *lactobacillus*.

* * * * *